(12) United States Patent
Gao et al.

(10) Patent No.: US 11,574,122 B2
(45) Date of Patent: Feb. 7, 2023

(54) METHOD AND SYSTEM FOR JOINT NAMED ENTITY RECOGNITION AND RELATION EXTRACTION USING CONVOLUTIONAL NEURAL NETWORK

(71) Applicant: SHENZHEN KEYA MEDICAL TECHNOLOGY CORPORATION, Shenzhen (CN)

(72) Inventors: Feng Gao, Seattle, WA (US); Changsheng Liu, Pittsburgh, PA (US); Yue Pan, Seattle, WA (US); Youbing Yin, Kenmore, WA (US); Kunlin Cao, Kenmore, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 630 days.

(21) Appl. No.: 16/544,837

(22) Filed: Aug. 19, 2019

(65) Prior Publication Data
US 2020/0065374 A1 Feb. 27, 2020

Related U.S. Application Data

(60) Provisional application No. 62/721,608, filed on Aug. 23, 2018.

(51) Int. Cl.
*G06F 40/295* (2020.01)
*G06N 3/08* (2006.01)
*G16H 10/60* (2018.01)

(52) U.S. Cl.
CPC ............ *G06F 40/295* (2020.01); *G06N 3/08* (2013.01); *G16H 10/60* (2018.01)

(58) Field of Classification Search
None
See application file for complete search history.

(56) References Cited

U.S. PATENT DOCUMENTS

2018/0082183 A1* 3/2018 Hertz ................... G06N 5/00
2018/0157664 A1* 6/2018 Howell ................. G06N 7/005
(Continued)

OTHER PUBLICATIONS

Giannis Bekoulis, Joint entity recognition and relation extraction as a multi-head selection problem, Apr. 20, 2018, arXiv:1804.07847v1 (Year: 2018).*

(Continued)

*Primary Examiner* — Antim G Shah
(74) *Attorney, Agent, or Firm* — Bayes PLLC (57) ABSTRACT

Embodiments of the disclosure provide systems and methods for processing unstructured texts in a medical record. A disclosed system includes at least one processor configured to determine a plurality of word representations of an unstructured text and tag entities in the unstructured text by performing a named entity recognition task on the plurality of word representations. The at least one processor is further configured to determine position embeddings based on positions of words in the unstructured text relative to positions of the tagged entities and concatenate the plurality of word representations with the position embeddings. The at least one processor is also configured to determine relation labels between pairs of tagged entities by performing a relationship extraction task on the concatenated word representations and position embeddings.

19 Claims, 6 Drawing Sheets

(56) References Cited

U.S. PATENT DOCUMENTS

2019/0318726 A1* 10/2019 Jin .......................... G10L 15/16
2020/0034435 A1* 1/2020 Norouzi .................. G06F 40/44

OTHER PUBLICATIONS

Xishuang Dong, A Multiclass Classification Method Based on Deep Learning for Named Entity Recognition in Electronic Medical Records, 2016, IEEE, 978-1-4673-9051-4/16/, pp. 1-10 (Year: 2016).*

Qiyan Xu, Joint Learning of Named Entity Recognition and Relation Extraction, 2011, 2011 International Conference on Computer Science and Network Technology, IEEE Xplore, pp. 1979-1982. (Year: 2011).*

Fei Li, A neural joint model for entity and relation extraction from biomedical text, 2017, BMC Bioinformatics, pp. 1-9. (Year: 2017).*

* cited by examiner

METHOD AND SYSTEM FOR JOINT NAMED ENTITY RECOGNITION AND RELATION EXTRACTION USING CONVOLUTIONAL NEURAL NETWORK

CROSS-REFERENCE TO RELATED APPLICATION

This application claims the benefit of priority to U.S. Provisional Application No. 62/721,608, filed on Aug. 23, 2018, the entire content of which is incorporated herein by reference.

TECHNICAL FIELD

The present disclosure relates to systems and methods for medical record processing, and more particularly to, systems and methods for medical record processing using joint named entity recognition (NER) and relation extraction (RE) using a convolutional neural network (CNN).

BACKGROUND

Natural Language Processing (NLP) has been widely used in the medical domain to automatically extract useful information. NER and RE from unstructured text are fundamental tasks in many important NLP information extraction applications. For example, such tasks may include medical report structuring and biomedical text mining using free texts such as electronic medical records and biomedical research articles.

Traditional NER and RE methods are heavily dependent on hand-crafted features and language-specific lexical resources such as gazetteers and require a large amount of domain knowledge. Over the past few years, the development of deep neural networks has enabled automatic learning of features, which freed the time-consuming process of creating hand-crafted features. However, existing NER and RE methods still have many drawbacks. For example, a NER task typically employs a bi-directional recurrent neural network (RNN), e.g., LSTM or GRU, for sequential encoding and a conditional random field (CRF) network for decoding. However, RNN is slow to train and its capability to capture long range dependency is limited in sequence-to-sequence learning tasks. In addition, word embedding is a typical and crucial input for such models. However, a potential limitation of using only word-level information is the incapability to encode orthographic information in entities. Although it has been proposed to extend word embedding with character-level information using neural networks to improve NER performance, no character-level model has been developed that can effectively capture character-level information. On the other hand, the RE task typically utilizes a syntactic dependency parser to exploit the dependency relations among words in context. There are two main problems with this approach: (1) dependency parser is not always available in the medical domain, and the use of dependency parsers from another domain will strongly limit its accuracy and value; (2) such models are not end-to-end trainable, namely dependency parsers need to be pre-trained and its results will be used as input to the RE model.

Furthermore, in the existing methods, NER and RE are typically applied in sequence, i.e., NER is performed first and the results are used as inputs to the RE task. Such pipeline methods suffer from error propagation.

Embodiments of the disclosure address the above problems by systems and methods for joint NER and RE using a CNN.

SUMMARY

In one aspect, embodiments of the disclosure provide a system for processing unstructured texts in a medical record. The system includes at least one processor configured to determine a plurality of word representations of an unstructured text and tag entities in the unstructured text by performing a named entity recognition task on the plurality of word representations. The at least one processor is further configured to determine position embeddings based on positions of words in the unstructured text relative to positions of the tagged entities and concatenate the plurality of word representations with the position embeddings. The at least one processor is also configured to determine relation labels between pairs of tagged entities by performing a relationship extraction task on the concatenated word representations and position embeddings.

In another aspect, embodiments of the disclosure also provide a method for processing unstructured texts in a medical record. The method includes determining, by at least one processor, a plurality of word representations of an unstructured text and tagging entities in the unstructured text by performing a named entity recognition task on the plurality of word representations. The method further includes determining, by the at least one processor, position embeddings based on positions of words in the unstructured text relative to positions of the tagged entities and concatenating the plurality of word representations with the position embeddings. The method also includes determining, by the at least one processor, relation labels between pairs of tagged entities by performing a relationship extraction task on the concatenated word representations and position embeddings.

In yet another aspect, embodiments of the disclosure further provide a non-transitory computer-readable medium having instructions stored thereon that, when executed by at least one processor, causes the at least one processor to perform a method for processing unstructured texts in a medical record. The method includes determining a plurality of word representations of an unstructured text and tagging entities in the unstructured text by performing a named entity recognition task on the plurality of word representations. The method further includes determining position embeddings based on positions of words in the unstructured text relative to positions of the tagged entities and concatenating the plurality of word representations with the position embeddings. The method also includes determining relation labels between pairs of tagged entities by performing a relationship extraction task on the concatenated word representations and position embeddings.

It is to be understood that both the foregoing general description and the following detailed description are exemplary and explanatory only and are not restrictive of the invention, as claimed.

DETAILED DESCRIPTION

Reference will now be made in detail to the exemplary embodiments, examples of which are illustrated in the accompanying drawings.

The disclosed systems and methods use a joint, end-to-end trainable deep learning network for NER and RE. The disclosed systems and methods can be used for processing unstructured texts. For example, they can be applied to construct a medical report or conduct medical record mining by extracting information from unstructured texts in medical records. Two learning tasks, a NER and a RE, are performed conjunctively to reduce error propagation and improve performance. For the NER task, various types of word representations of an unstructured text are determined first. In some embodiments, these word representations may include subword representations, dilated subword representations, capitalization representations, and word embeddings. For example, the disclosed approach embeds a novel attention-based subword encoder to capture character-level features automatically. The NER then tags the entities in the unstructured text based on the various types of word representations. For the RE task, position embeddings are determined first based on positions of words in the unstructured text relative to positions of the tagged entities. The position embeddings and then concatenated with the word representations. RE is applied to determine relation labels between pairs of tagged entities based on the concatenated word representations and position embeddings.

With the disclosed joint NER and RE approach, the shared parameters between the two components enable interaction during training and improve the performance on both tasks. In some embodiments, the disclosed approach can be completely based on CNN rather than RNN such as LSTM and GRU. Training a CNN is generally faster than training an RNN and the CNN training is GPU parallelizable. In some embodiments, the disclosed NER task adopts an embedded attention mechanism which can automatically learn to focus on important subwords in a word. This also enables visualization of the results. In some additional embodiments, the disclosed RE task adopts an embedded attention mechanism which can automatically learn to focus on important words without use of third-party dependency parser, which relies on external information and needs to be pre-trained.

Figure 1:
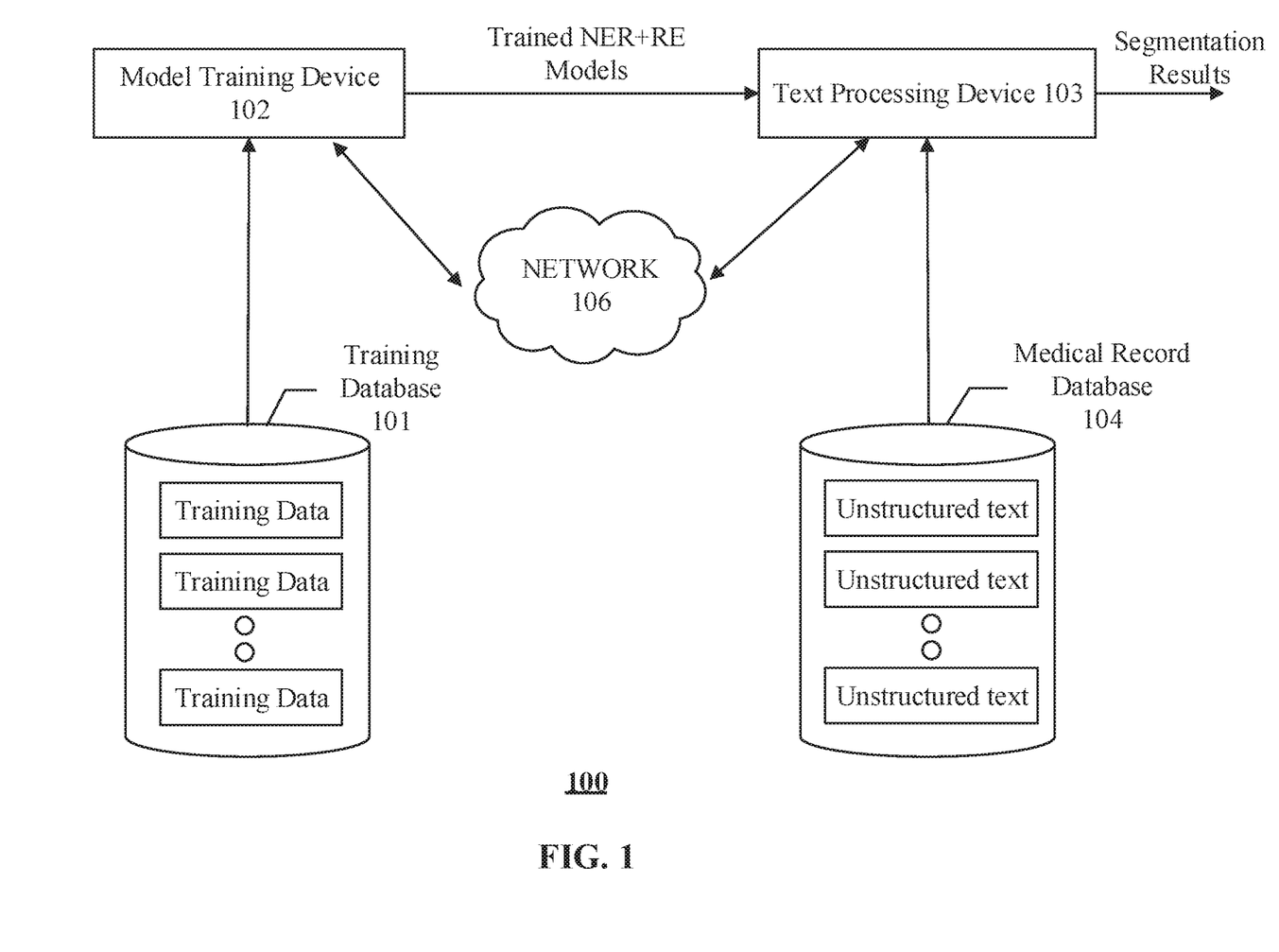
FIG. 1 illustrates a schematic diagram of an exemplary text processing system, according to embodiments of the disclosure.

FIG. 1 illustrates an exemplary text processing system 100, according to some embodiments of the present disclosure. Consistent with the present disclosure, text processing system 100 is configured to process and extract information from unstructured texts in a medical record. For example, the unstructured texts may be free texts from electronic medical records and biomedical research articles. In some embodiments, text processing system 100 is further configured to construct a medical report or perform biomedical text mining based on the extracted information.

As shown in FIG. 1, text processing system 100 may include components for performing two phases, a training phase and a prediction phase. To perform the training phase, text processing system 100 may include a training database 101 and a model training device 102. The training phase may be exploited to train a learning model (also known as a "learning network") for processing unstructured texts. To perform the prediction phase, text processing system 100 may include a text processing device 103 and a medical record database 104. In some embodiments, text processing system 100 may include more or less of the components shown in FIG. 1. For example, when the learning model for processing the texts is pre-trained and provided, text processing system 100 may include only text processing device 103 and medical record database 104.

Text processing system 100 may optionally include a network 106 to facilitate the communication among the various components of text processing system 100, such as databases 101 and 104, and devices 102 and 103. For example, network 106 may be a local area network (LAN), a wireless network, a cloud computing environment (e.g., software as a service, platform as a service, infrastructure as a service), a client-server, a wide area network (WAN), etc. In some embodiments, network 106 may be replaced by wired data communication systems or devices.

In some embodiments, the various components of text processing system 100 may be remote from each other or in different locations, and be connected through network 106 as shown in FIG. 1. In some alternative embodiments, certain components of text processing system 100 may be located on the same site or inside one device. For example, training database 101 may be located on-site with or be part of model training device 102. As another example, model training device 102 and text processing device 103 may be inside the same computer or processing device.

Model training device 102 may use the training data received from training database 101 to train a text processing model for extracting information from unstructured texts in a medical record received from, e.g., medical record database 104. In some embodiments, the text processing model may be a deep learning model that has a large number of layers. In some embodiments, the text processing model may be a joint NER and RE model, which includes a NER component and a RE component. Consistent with the present disclosure, NER (also known as entity identification, entity chunking or entity extraction), is a subtask of information extraction that seeks to locate and classify named entity mentions in unstructured text into pre-defined categories. NER tags words or phrases in the unstructured text with named entity s, such as the person names, organizations, locations, medical codes, time expressions, quantities, monetary values, percentages, etc. Consistent with the present disclosure, RE is the task of extracting semantic relationships from a text. In some embodiments, the extracted relationships may occur between two or more named entities tagged by a NER task (e.g., between a person name and an organization). The extracted relationship may itself fall into a number of semantic categories, e.g., married to, employed by, lives in, happened during, etc. RE produces relation labels for the different semantic categories of the extracted relationships.

As shown in FIG. 1, model training device 102 may communicate with training database 101 to receive one or more sets of training data. Each set of training data may include a training text and its corresponding named entity tags and relation labels. The training texts may be unstructured texts that do not have a pre-defined data structure or not organized in a pre-defined manner. Unstructured texts usually lack metadata and cannot readily be indexed or mapped onto standard database fields. They are often user-generated information such as email or instant messages, documents or social media postings. In some embodiments, training texts stored in training database 101 may be unstructured texts obtained from a medical record database containing electronic medical records from clinics and hospitals as well as public medical articles such as journal papers or conference papers.

In some embodiments, the ground truth can be named entity tags and relation labels for the training texts. The training texts are previously analyzed or annotated by operators or computers with the named entities tagged and their relationships labeled. As one example, NER can use the BIOES (Begin, Inside, Outside, End, Single) tagging scheme. For example, if there are two entity tags T1 and T2, all available labels are {B-T1, I-T1, O-T1, E-T1, S-T1, B-T2, I-T2, O-T2, E-T2, S-T2}, and each word will be assigned such a label. As another example, training text "Jim had a bypass heart surgery at the Massachusetts General Hospital in 2010" can be tagged as:

[Jim]$_{person}$ had a [bypass heart surgery]$_{treatment\ name}$ at the [Massachusetts General Hospital]$_{organization}$ in [2010]$_{time}$ And the corresponding relation labels may be as follows:
(operated on, Bypass Heart Surgery, Jim)
(treated in, Jim, Massachusetts General Hospital)
(happened during, Bypass Heart Surgery, 2010)

The aim of the training phase is to learn a mapping between the training texts and the ground truth entity tags and relation labels by finding the best fit between predictions and ground truth values over the sets of training data. In some embodiments, the training phase may be performed "online" or "offline." An "online" training refers to performing the training phase contemporarily with the prediction phase, e.g., learning the model in real-time just prior to processing a text. An "online" training may have the benefit to obtain a most updated learning model based on the training data that is then available. However, an "online" training may be computational costive to perform and may not always be possible if the training data is large and/or the model is complicate. Consistent with the present disclosure, an "offline" training is used where the training phase is performed separately from the prediction phase. The learned model trained offline is saved and reused for text processing.

Model training device 102 may be implemented with hardware specially programmed by software that performs the training process. For example, model training device 102 may include a processor and a non-transitory computer-readable medium (discussed in detail in connection with FIG. 3). The processor may conduct the training by performing instructions of a training process stored in the computer-readable medium. Model training device 102 may additionally include input and output interfaces to communicate with training database 101, network 106, and/or a user interface (not shown). The user interface may be used for selecting sets of training data, adjusting one or more parameters of the training process, selecting or modifying a framework of the learning model, and/or manually or semi-automatically providing prediction results associated with an unstructured text for processing.

Consistent with some embodiments, the text processing model may be a machine learning model that include at least two components: a NER network configured to tag the named entities in the unstructured texts and a RE network configured to label the relationships between the named entities.

Figure 2:
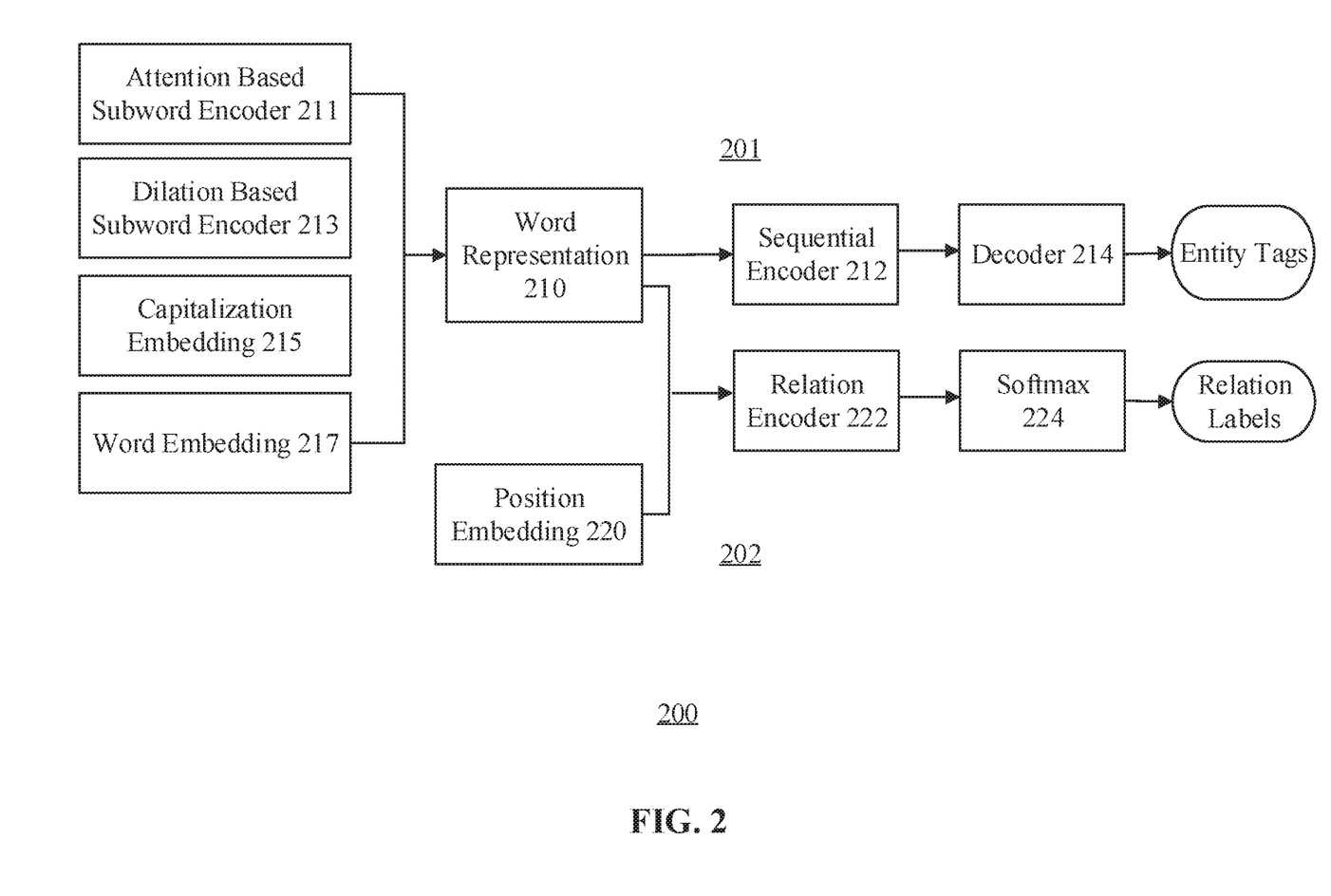
FIG. 2 illustrates an exemplary joint named entity recognition and relation extraction network, according to embodiments of the disclosure.

FIG. 2 illustrates an exemplary joint named entity recognition and relation extraction network (hereafter, "joint NER and RE network") 200, according to embodiments of the disclosure. As shown by FIG. 2, joint NER and RE network may include a NER network 201 for predicting named entity tags and a RE network 202 for predicting relation labels. In some embodiments, NER network 201 may include several layers, such as a word representing layer 210 where several types of representations are determined, a sequential encoder layer 212, and a decoding layer 214. In some embodiments, word representation layer 210 may further include an attention-based subword encoder sublayer 211, a dilation-based subword encoder sublayer 213, a capitalization embedding sublayer 215, and a word embedding sublayer 217. In some embodiments, as shown by FIG. 2, RE network 202 may also include several layers, such as a position embedding layer 220, a relation encoder layer 222, and a softmax layer 224. In some embodiments, RE network 202 may share word representation layer 210 with NER 201.

Figure 3:
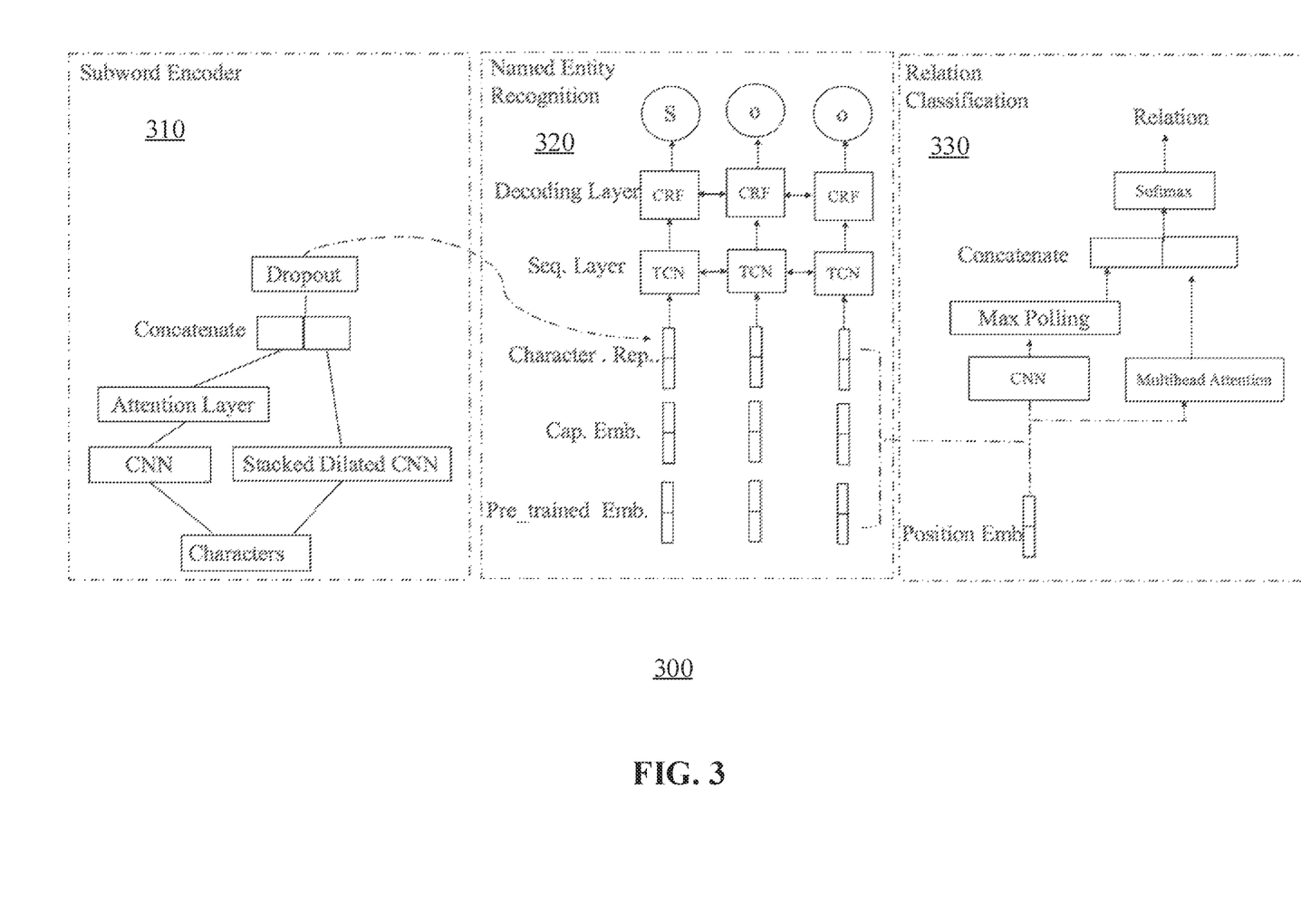
FIG. 3 illustrates an exemplary implementation of the joint named entity recognition and relation extraction network of FIG. 2, according to embodiments of the disclosure.

FIG. 3 illustrates an exemplary implementation of the joint named entity recognition and relation extraction network 200 of FIG. 2, according to embodiments of the disclosure. FIG. 3 shows implementations of three components joint NER and RE network 200: a subword encoder component 310, a NER component 320, and a relation classification component 330. Subword encoder component 310 may include attention-based subword encoder sublayer 211 and dilation-based subword encoder sublayer 213, both providing subword representations of the unstructured text.

In some embodiments, as shown in FIG. 3, attention-based subword encoder sublayer 211 may first apply a CNN on subwords (e.g., characters) within a word to capture subword information. For example, attention-based subword encoder sublayer 211 may first break a word down into characters. These characters are then mapped to a sequence of embeddings, which may be retrieved from the look up table of char embedding. A CNN layer is applied on top of this embedding sequence.

In some embodiments, attention-based subword encoder sublayer 211 is designed to differentiate these subwords and explicitly considering their importance. For example, attention-based subword encoder sublayer 211 may employ an attention layer over the output of CNN, which will enable the model to learn salient subwords automatically. In one implementation, the attention layer will generate an importance score for each subword based on the dot product of the attention weight vector and the encoding of the subword. The score may be further normalized using a softmax function.

Attention-based subword representation models each subword separately, which could lead to high false positives. To compensate for that, in some embodiments, dilation-based subword encoder sublayer 213 is included to provide an overall representation of the characters within a word using dilated CNN. Dilated convolutions perform the same operation as standard CNN. However, instead of transforming directly adjacent inputs, the dilated convolution is operated over a wider input window by skipping over a constant number of inputs at a time. The index difference between two consecutive input of dilated convolution is a dilation factor. The standard CNN can be considered as a dilated convolution with dilation factor equal to 1. When the dilation factor is larger than 1, dilated convolution can incorporate broader context into the representation of a token than a standard CNN. In some embodiments, dilation-based subword encoder sublayer 213 may stacking many dilated CNN layers to incorporate information from a whole sequence. The dilated CNN is used to build an overall character level representation to jointly model all the characters in the word.

Subword encoder component 310 may be incorporated into NER component 320 to determine its subword/character representations. In some embodiments, NER component 320 further include capitalization embedding sublayer 215 to determine capitalization representations. Capitalization is a key orthographic feature for recognizing named entities. A word's case information is categorized into four types: (1) all characters are lowercases; (2) all are uppercases; (3) first character is uppercase; (4) one or more characters but not the first is capital. In some embodiments, each type may be mapped to a vector which is initialized with random numbers. A by-product of lowering case of words is that it can reduce the size of word vocabulary and reduce sparsity. In some embodiments, the complete character-level representation is the concatenation of attention-based subword representation, capitalization representation and dilation-based subword representation.

In some embodiments, NER component 320 further include word embedding sublayer 217. Word embedding is another component in word representation. In some embodiments, pre-trained word embeddings can be used. In some other embodiments, randomly-initialized word embeddings can be used. The word embedding process may be fine-tuned during training process.

NER component 320 also includes sequential encoding layer 212 and decoding layer 214. In some embodiments, sequential encoding may be implemented as a bi-directional temporal convolution network (TCN). In some embodiments, decoding layer 214 may be implemented as a CRF to generate a probability distribution over sequences of tags. That is, CRF decoding assigns a probability to each possible named entity and the one with the highest probability becomes the named entity tag output by decoding layer 214. For example, the probability of the word/phrase falls in the categories of a person name, organization, location, medical code, time expression, quantity, monetary value, percentage, etc. may be determined, and the category with the highest probability may be used to tag the word/phrase.

Relation classification component 330 may include position embedding layer 220. In some embodiments, the position embedding is based on the relative distance of the current word to the target entity. Words close to the entities are important for relation classification. In some embodiments, the disclosed RE model uses word position embeddings to help the model keep track of how close words are to the target entities. In some embodiments, each distance may be mapped to a vector that will be updated during training. In some embodiments, when there are two entities, for each word in context, two position embeddings are obtained corresponding to the two entities. The concatenation of the two embeddings may be used as the final position embedding.

Relation classification component 330 further include relation encoder layer 222. In some embodiments, the input to relation encoder layer 222 may be the concatenation of the aforementioned word representation in NER component 320 and the position embedding provided by position embedding layer 220. In this way, relation classification component 330 shares the same word representation parameters with NER component 320. For example, the shared word representations may include one or more of the attention-based sub-word representations provided by attention-based subword encoder sublayer 211, the dilation-based subword representations provided by dilation-based subword encoder sublayer 213, the capitalization representation provided by capitalization embedding sublayer 215, and the word embedding provided by word embedding sublayer 217. In some embodiments, the input may be first fed to a convolutional layer (e.g., a CNN) to generate a set of vector representations of short phrases in the sentence. In some embodiments, a max pooling layer is added to extract the most salient features. In some embodiments, an attention layer may be also applied to the input layer directly to learn those critical words for relation classification. For example, the attention layer may be a multihead attention layer. In some embodiments, the importance score for each word in the attention mechanism may be based on the dot product of the attention vector and the vector representation of the word. The importance score may be then normalized before being assigned as the weight for each word. The attention layer may output the weighted sum of input vectors. In some embodiments, the output of relation encoder layer is 222 may be the concatenation of the output of the max pooling layer and the attention layer.

Relation classification component 320 further includes softmax layer 224 to predict the relation labels based on the output of relation encoder layer is 222. Softmax assigns decimal probabilities to each class in a multi-class problem. Those decimal probabilities must add up to 1.0. That is, softmax layer 224 assigns a probability to each possible relation label and the label that associated with the highest probability becomes the label of the relationship between named entities. For example, the probability of the word/phrase falls in the categories of a person name, organization, location, medical code, time expression, quantity, monetary value, percentage, etc. may be determined, and the category with the highest probability may be used to tag the word/phrase.

In some embodiments, model training device 102 trains joint NER and RE network 200, including NER network 201 and RE network 202, using the training data from training database 101. In some embodiments, NER network 201 and RE network 202 may be trained separately. In some embodiments consistent with the present disclosure, the end-to-end network including both NER network 201 and RE network 202 may be trained jointly as one piece rather than separately. Because NER network 201 and RE network 202 share the same word representations, training them jointly reduces error propagation between the two networks. Therefore, when later used to process a new unstructured text, joint NER and RE network 200 can be more reliable.

As used herein, "training" a learning model refers to determining one or more parameters of at least one layer in the learning model. For example, a convolutional layer of an CNN model may include at least one filter or kernel. One or more parameters, such as kernel weights, size, shape, and structure, of the at least one filter may be determined by e.g., a backpropagation-based training process. Joint NER and RE network 200 may be trained using supervised learning, semi-supervised learning, or unsupervised learning.

In some embodiments, the training may use a joint-loss function accounting for losses from both the NRE part and the RE part, such as a weighted average of the two losses. For example, cross-entropy loss can be used as the loss function for both the NRE part and the RE part. In some embodiments, Adam optimizer can be used for optimizing the model parameters.

Returning to FIG. 1, the trained segmentation model may be used by text processing device 103 to extract information from new unstructured texts. Text processing device 103 may receive the text processing model, e.g., joint NER and RE network 200, from model training device 102. Text processing device 103 may include a processor and a non-transitory computer-readable medium (discussed in detail in connection with FIG. 3). The processor may perform instructions of an unstructured text processing process stored in the medium. Text processing device 103 may additionally include input and output interfaces (discussed in detail in connection with FIG. 3) to communicate with medical record database 104, network 106, and/or a user interface (not shown). The user interface may be used for selecting an unstructured text for processing, initiating the process, and displaying the processing results.

Text processing device 103 may communicate with medical record database 104 to receive one or more unstructured texts. In some embodiments, the unstructured texts stored in medical record database 104 may include free texts from electronic medical records or medical research articles. Text processing device 103 may then uses the trained text processing model received from model training device 102 to tag the named entities within the text and predict relation labels between the tagged named entities.

Figure 4:
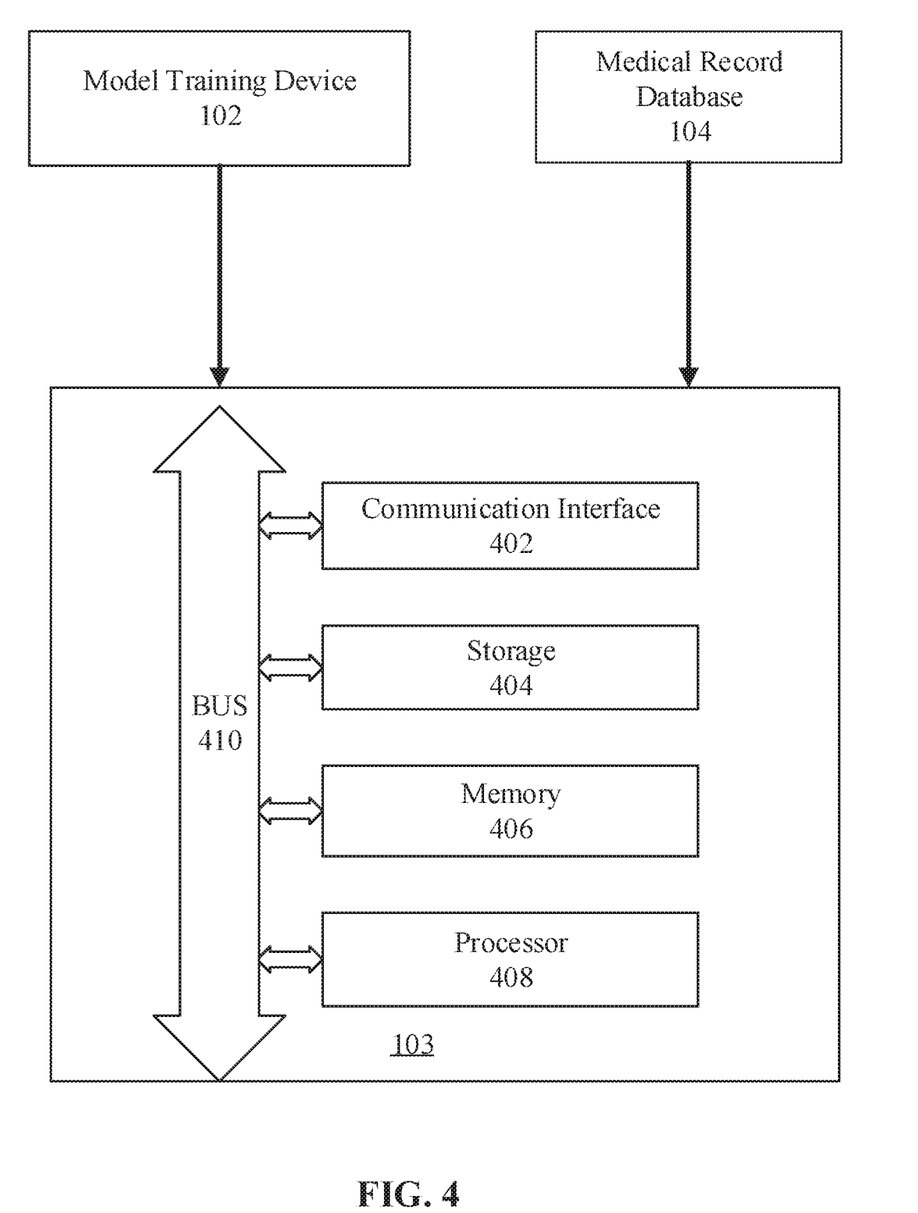
FIG. 4 illustrates a block diagram of an exemplary text processing device, according to embodiments of the disclosure.

FIG. 4 illustrates an exemplary text processing device 103, according to some embodiments of the present disclosure. In some embodiments, text processing device 103 may be a special-purpose computer, or a general-purpose computer. For example, text processing device 103 may be a computer custom-built for hospitals to perform medical record processing tasks. As shown in FIG. 4, text processing device 103 may include a communication interface 402, a storage 404, a memory 406, a processor 408, and a bus 410. Communication interface 402, storage 404, memory 406, and processor 408 are connected with bus 410 and communicate with each other through bus 410.

Communication interface 402 may include a network adaptor, a cable connector, a serial connector, a USB connector, a parallel connector, a high-speed data transmission adaptor, such as fiber, USB 3.0, thunderbolt, and the like, a wireless network adaptor, such as a WiFi adaptor, a telecommunication (3G, 4G/LTE and the like) adaptor, etc. Text processing device 103 may be connected to other components of text processing system 100 and network 106 through communication interface 402. In some embodiments, communication interface 402 receives unstructured texts from medical record database 104. In some embodiments, communication interface 402 also receives the text processing model, e.g., joint NER and RE network 200, from modeling training device 102.

Storage 404/memory 406 may be a non-transitory computer-readable medium, such as a read-only memory (ROM), a random access memory (RAM), a phase-change random access memory (PRAM), a static random access memory (SRAM), a dynamic random access memory (DRAM), an electrically erasable programmable read-only memory (EEPROM), other types of random access memories (RAMs), a flash disk or other forms of flash memory, a cache, a register, a static memory, a compact disc read-only memory (CD-ROM), a digital versatile disc (DVD) or other optical storage, a cassette tape or other magnetic storage devices, or any other non-transitory medium that may be used to store information or instructions capable of being accessed by a computer device, etc.

In some embodiments, storage 404 may store the trained learning model, e.g., joint NER and RE network 200, and data, such as the unstructured texts and various word representations and position embeddings generated while executing the computer programs, etc. In some embodiments, memory 406 may store computer-executable instructions, such as one or more text processing programs. In some embodiments, multiple types of word presentations, including, e.g., attention-based subword representation, dilation-based subword representation, capitalization representation, and word embedding (either pretrained or randomly initialized), may be determined and stored in storage 404. The word representations may be read from storage 404 one by one or simultaneously and stored in memory 406 to be feed to subsequent layers of NER or RE network.

Processor 408 may be a processing device that includes one or more general processing devices, such as a microprocessor, a central processing unit (CPU), a graphics processing unit (GPU), and the like. More specifically, the processor may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The processor may also be one or more dedicated processing devices such as application specific integrated circuits (ASICs), field programmable gate arrays (FPGAs), digital signal processors (DSPs), system-on-chip (SoCs), and the like. Processor 408 may be communicatively coupled to memory 406 and configured to execute the computer-executable instructions stored thereon.

In some embodiments, processor 408 is configured to extract information from unstructured texts in a medical record. For example, processor 408 first determine word representations of the unstructured text. In some embodiments, processor 408 may determine one or more of an attention-based subword representation, dilation-based subword representation, capitalization representation, and word embedding. Processor 408 then tags entities in the unstructured text by performing a named entity recognition task on the word representations. Processor 408 may determine position embeddings based on positions of words in the unstructured text relative to positions of the tagged entities. In some embodiments, processor 408 concatenates the plurality of word representations with the position embeddings and determine relation labels between pairs of tagged entities by performing a relationship extraction task on the concatenated word representations and position embeddings. An exemplary text processing method performed by processor 408 will be described in connection with FIG. 6.

Consistent with the present disclosure, model training device 102 can have same or similar structures as text processing device 103. In some embodiments, model training device 102 includes a processor, among other components, configured to train joint NER and RE network 200 using training data from training database 101. An exemplary network training process will be described in connection with FIG. 5.

Figure 5:
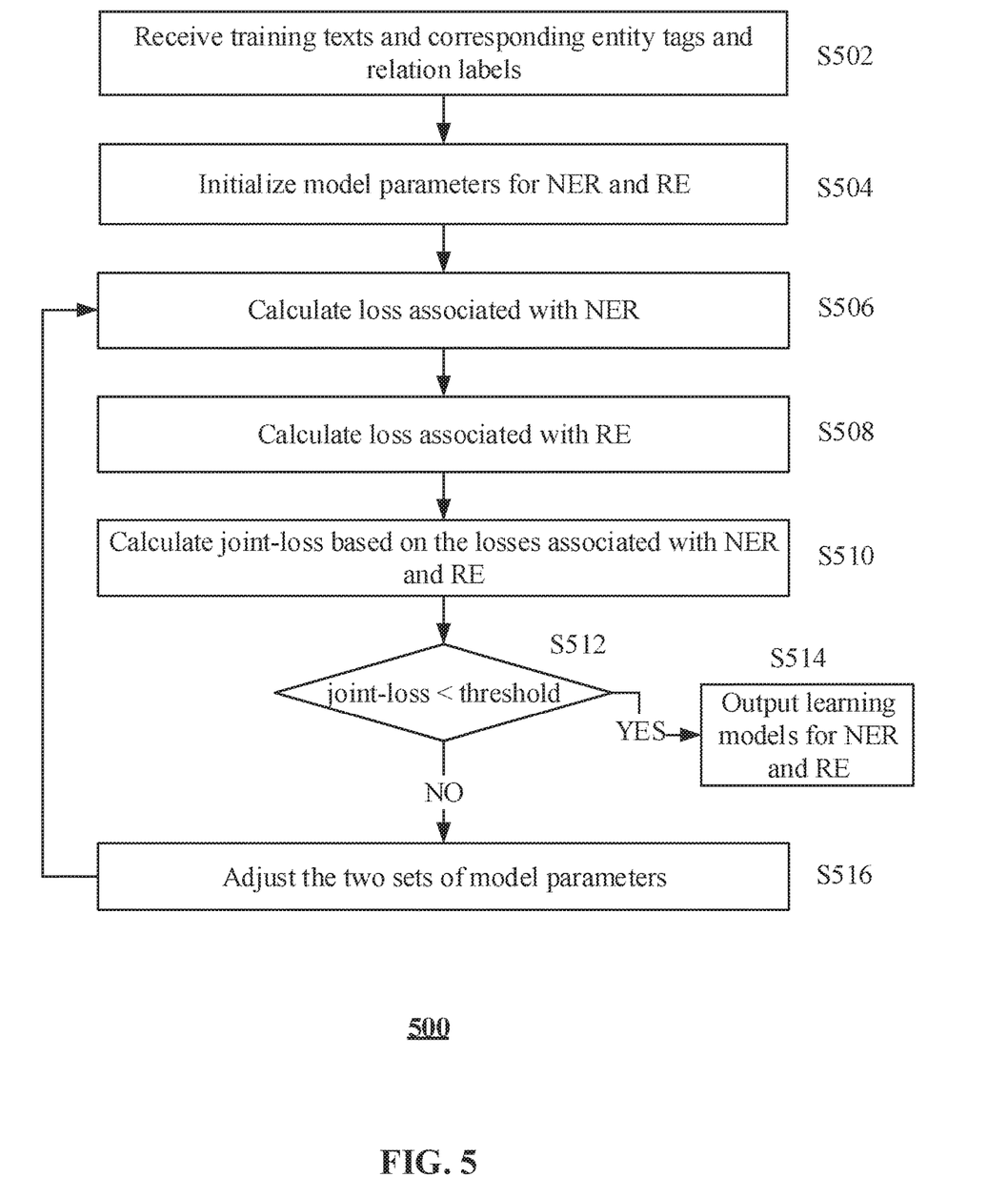
FIG. 5 is a flowchart of an exemplary method for training a joint named entity recognition and relation extraction network, according to embodiments of the disclosure.

FIG. 5 is a flowchart of an exemplary method 500 for training joint named entity recognition and relation extraction network 200, according to embodiments of the disclosure. For example, method 500 may be implemented by model training device 102 in FIG. 1. However, method 500 is not limited to that exemplary embodiment. Method 500 may include steps S502-S516 as described below. It is to be appreciated that some of the steps may be optional to perform the disclosure provided herein. Further, some of the steps may be performed simultaneously, or in a different order than shown in FIG. 5.

In step S502, model training device 102 may communicate with training database 101 to receive one or more sets of training data. Each set of training data may include a training text from a medical record and its corresponding ground truth entity tags and relation labels.

In step S504, model training device 102 may initialize the parameters of joint NER and RE network 200. Training the learning model is a process of determining one or more parameters of the learning model. Consistent with the present disclosure, model training device 102 trains NER network 201 and RE network 202 with a joint loss function, using the training data from training database 101. The set of parameters of the two networks may be trained separately or jointly. For example, set of parameters of NER network 410 and set of parameters of RE network can be separately or jointly determined. The parameters may be initially set to certain values. The initial values may be predetermined, selected by an operator, or decided by model training device 102 based on prior experience of similar texts. For example, parameters of a learning model previously trained for unstructured textures from medical research article A may be used as initial values for the parameters of the learning model being trained for unstructured textures from medical research article B.

In steps 506 and 508, model training device 102 may calculate a loss associated with NER and a loss associated with RE, respectively. In some embodiments, the losses may be calculated according to a loss function. In one embodiment, the training may use a joint-loss function accounting for losses for this joint NER and RE training. For example, the loss function may be a weighted average of the losses of the NER part and the RE part. For example, cross-entropy loss can be used as the loss function for both the NRE part and the RE part. In some embodiments, Adam optimizer can be used for optimizing the model parameters.

In step S510, model training device 102 may calculate a joint-loss based on the losses associated with the NER part and the RE part calculated in steps S506 and S508. In some embodiments, the joint loss may be calculated according to the joint loss function, e.g., the cross-entropy loss function. The losses associated with the NER part and the RE part may be weighted according to the importance of the two parts. For example, the joint-loss may be calculated as a weighted average of the losses of the NER part and the RE part.

In step S512, the calculated joint loss may be compared with a predetermined threshold. The predetermined threshold is also known as the stopping criteria for interactive methods. The smaller it is, the more optimal the parameters, but the longer it takes (i.e., more iterations) for the computation to converge. Therefore, the threshold may be selected to balance the accuracy of the prediction and the computational cost.

If the value is below the predetermined threshold (step S512: Yes), the method is considered as have converged, and the cost function is minimized. In step S514, model training device 102 outputs the learning model with the optimized sets of parameters and method 600 concludes. Otherwise (step S512: No), model training device 102 may further adjust the two sets of parameters jointly in step S514. In some embodiments, Adam optimizer can be used for optimizing model parameters. Adam is an adaptive learning rate optimization algorithm that has been designed specifically for training deep neural networks. The algorithm leverages the power of adaptive learning rates methods to find individual learning rates for each parameter.

Method 500 may return to step S506 to calculate loss of NER based on outputs obtained from the learning model with the adjusted sets of parameters. Each pass of steps S606-S612 is considered as one iteration. Method 600 iterates until the value of the cost function is reduced to below the predetermined threshold (step S512).

Figure 6:
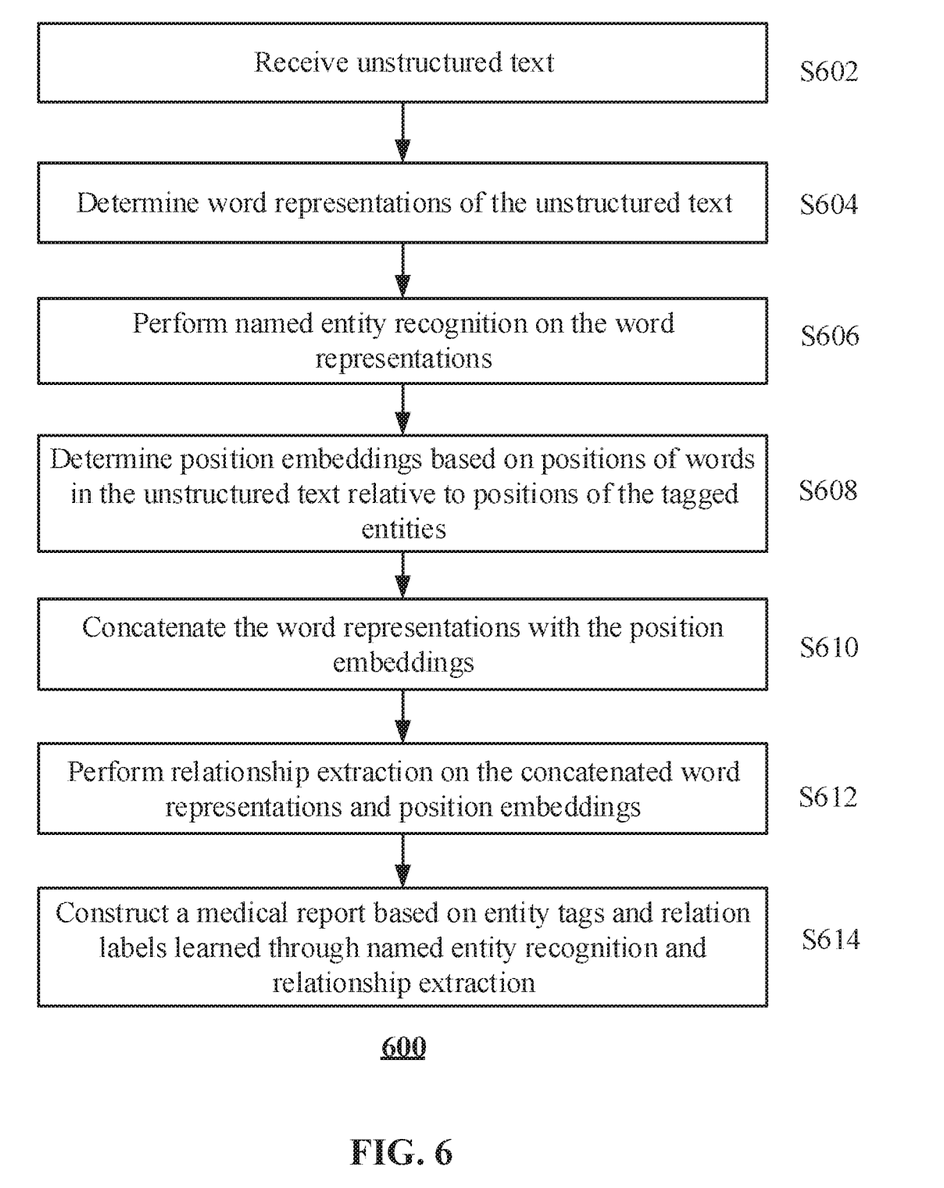
FIG. 6 is a flowchart of an exemplary method for processing unstructured texts using a joint named entity recognition and relation extraction network, according to embodiments of the disclosure.

FIG. 6 is a flowchart of an exemplary method 600 for processing unstructured texts using a joint named entity recognition and relation extraction network 200, according to embodiments of the disclosure. For example, method 600 may be implemented by text processing device 103 in FIG. 1. However, method 600 is not limited to that exemplary embodiment. Method 600 may include steps S602-S614 as described below. It is to be appreciated that some of the steps may be optional to perform the disclosure provided herein. Further, some of the steps may be performed simultaneously, or in a different order than shown in FIG. 6.

In step S602, text processing device 103 receives an unstructured text, e.g., from medical record database 104. The unstructured text may be part of an electronic medical record or a medical research article. Text processing device 103 may additionally receive a text processing model, e.g., joint NER and RE network 400. The text processing model may be trained using method 500.

In step S604, text processing device 103 determines various word representations of the unstructured text, e.g., using word representation layer 210 of joint NER and RE network 200. In some embodiments, text processing device 103 may determine one or more of the attention-based subword representations using attention-based subword encoder sublayer 211, the dilation-based subword representations using dilation-based subword encoder sublayer 213, the capitalization representation using capitalization embedding sublayer 215, and the word embedding using word embedding sublayer 217. In some embodiments, a CNN may be applied to determine the attention-based subword representations. In some embodiments, an attention layer may be applied on top of the CNN to learn salient subwords automatically. For example, the attention layer may generate an importance score for each subword based on the dot product of the attention weight vector and the encoding of the subword. In some embodiments, a dilated CNN with a dilation factor larger than 1 may be applied to the input to provide an overall representation of the characters within a word.

In step S606, text processing device 103 performs NER on the word representations, e.g., using sequential encoding layer 212 and decoding layer 214 of joint NER and RE network 200. In some embodiments, sequential encoding may be implemented as a bi-directional temporal convolution network (TCN). In some embodiments, decoding layer 214 may be implemented as a CRF to generate a probability distribution over sequences of tags.

In step S608, text processing device 103 determines position embeddings based on positions of words in the unstructured text relative to positions of the tagged entries, e.g., using position embedding layer 220 of joint NER and RE network 200. In some embodiments, the relative distance of the current word to each target entity is calculated and mapped to a vector that will be updated during training. In some embodiments, when there are two entities, for each word in context, two position embeddings are obtained corresponding to the two entities and then concatenated to form the final position embedding for the word.

In step S610, text processing device 103 concatenates the word representations determined in step S604 with the position embeddings determined in step S608. In step S612, text processing device 103 performs RE on the concatenated word representations and position embeddings. In this way, RE shares the same word representation parameters with NER. In some embodiments, text processing device 103 may perform the RE using relation encoder layer 222 and softmax layer 224 of joint NER and RE network 200. In some embodiments, the relation encoder may include a CNN to generate a set of vector representations of short phrases in the sentence and a max pooling layer to extract the most salient features. In some embodiments, the relation encoder may further include an attention layer to learn those critical words. In some embodiments, the attention layer may calculate an importance score for each word based on the dot product of the attention vector and the vector representation of the word. In some embodiments, the output of the max pooling layer and the output of the attention layer may be the concatenated and feed into softmax layer 224 to produce relation labels indicating relationships between tagged entities.

In step S614, text processing device 103 may further construct a medical report based on the entity tags and relation labels learned through steps S602-S614. In some embodiments, the medical report may contain texts describing a patient's medical history, symptoms, diagnosis, treatment plan, treatment history, lab data, etc. It will be appreciated by a person of ordinary skill in the art though the disclosed joint NER and RE approach can be adapted and applied to extracting information from unstructured texts in contexts other than a medical record.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A system for processing unstructured texts in a medical record, comprising:
at least one processor, configured to:
determine a plurality of word representations of an unstructured text, wherein the plurality of word representations comprise an attention-based subword representation determined by applying a convolutional neural network on subwords within words of the unstructured text and applying an attention layer over an output of the convolutional neural network;
tag entities in the unstructured text by performing a named entity recognition task on the plurality of word representations;
determine position embeddings based on positions of the words in the unstructured text relative to positions of the tagged entities;
concatenate the plurality of word representations with the position embeddings; and
determine relation labels between pairs of the tagged entities by performing a relation extraction task on the concatenated word representations and position embeddings,
wherein the named entity recognition task and the relation extraction task are performed by using the plurality of word representations as shared parameters to determine the tagged entities and the relation labels jointly.

2. The system of claim 1, wherein applying the convolutional neural network on the subwords within the words further includes:
breaking the words down to the subwords;
mapping the subwords to a sequence of embeddings; and
applying the convolutional neural network on the sequence of embeddings.

3. The system of claim 1, wherein applying the attention layer further comprises applying the attention layer over the output of the convolutional neural network to generate an importance score for each subword.

4. The system of claim 1, wherein the plurality of word representations include a capitalization representation indicative of whether the subwords within the words are uppercased or lowercased.

5. The system of claim 1, wherein the plurality of word representations include a dilated subword representation determined by applying a dilated convolutional neural network on the subwords within the words, wherein the dilated convolutional neural network has a dilation factor larger than 1.

6. The system of claim 1, wherein performing the named entity recognition task on the plurality of word representations further includes performing a sequential encoding to the plurality of word representations.

7. The system of claim 6, wherein performing the named entity recognition task on the plurality of word representations further includes performing a conditional random field decoding to the sequentially encoded word representations.

8. The system of claim 6, wherein the sequential encoding is performed using a bi-directional temporal convolution network.

9. The system of claim 6, wherein the at least one processor includes a graphic processing unit configured to perform the sequential encoding using parallel processing.

10. The system of claim 1, wherein the position embeddings are determined by:
calculating a distance between each word and each named entity; and
mapping the distance to a vector that is updated during training.

11. The system of claim 1, wherein performing the relation extraction task includes:
performing a relation encoding on concatenated word representations and position embeddings; and
applying a softmax layer to a result of the relation encoding to predict the relation labels.

12. The system of claim 11, wherein performing the relation encoding includes applying another attention layer configured to generate an importance score for each word in the unstructured text.

13. The system of claim 1, wherein the named entity recognition task and the relation extraction task are trained using a loss function designed to account for losses associated with both the named entity recognition task and the relation extraction task.

14. A method for processing unstructured texts in a medical record, comprising:
- determining, by at least one processor, a plurality of word representations of an unstructured text, wherein the plurality of word representations comprise an attention-based subword representation determined by applying a convolutional neural network on subwords within words of the unstructured text and applying an attention layer over an output of the convolutional neural network;
- tagging entities in the unstructured text by performing a named entity recognition task on the plurality of word representations;
- determining, by the at least one processor, position embeddings based on positions of the words in the unstructured text relative to positions of the tagged entities;
- concatenating the plurality of word representations with the position embeddings; and
- determining, by the at least one processor, relation labels between pairs of the tagged entities by performing a relation extraction task on the concatenated word representations and position embeddings,
- wherein the named entity recognition task and the relation extraction task are performed by using the plurality of word representations as shared parameters to determine the tagged entities and the relation labels jointly.

15. The method of claim 14, wherein applying the attention layer further comprises applying the attention layer over the output of the convolutional neural network to generate an importance score for each subword.

16. The method of claim 14, wherein performing the named entity recognition task on the plurality of word representations further includes:
- performing a sequential encoding to the plurality of word representations; and
- performing a conditional random field decoding to the sequentially encoded word representations.

17. The method of claim 14, wherein the plurality of word representations include a dilated subword representation determined by applying a dilated convolutional neural network on the subwords within the words, wherein the dilated convolutional neural network has a dilation factor larger than 1.

18. The method of claim 14, wherein the named entity recognition task and the relation extraction task are trained using a loss function designed to account for losses associated with both the named entity recognition task and the relation extraction task.

19. A non-transitory computer-readable medium having a computer program stored thereon, wherein the computer program, when executed by at least one processor, performs a method for processing unstructured texts in a medical record, the method comprising:
- determining a plurality of word representations of an unstructured text, wherein the plurality of word representations comprise an attention-based subword representation determined by applying a convolutional neural network on subwords within words of the unstructured text and applying an attention layer over an output of the convolutional neural network;
- tagging entities in the unstructured text by performing a named entity recognition task on the plurality of word representations;
- determining position embeddings based on positions of the words in the unstructured text relative to positions of the tagged entities;
- concatenating the plurality of word representations with the position embeddings; and
- determining relation labels between pairs of the tagged entities by performing a relation extraction task on the concatenated word representations and position embeddings,
- wherein the named entity recognition task and the relation extraction task are performed by using the plurality of word representations as shared parameters to determine the tagged entities and the relation labels jointly.

* * * * *